United States Patent
Beck et al.

(10) Patent No.: US 10,935,618 B2
(45) Date of Patent: Mar. 2, 2021

(54) MAGNETIC RESONANCE IMAGING USING ADDITIONAL GRADIENT PULSES

(71) Applicant: Siemens Healthcare GmbH, Erlangen (DE)

(72) Inventors: Thomas Beck, Erlangen (DE); Daniel Polak, Blankenbach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/665,304

(22) Filed: Oct. 28, 2019

(65) Prior Publication Data
US 2020/0132795 A1    Apr. 30, 2020

(30) Foreign Application Priority Data
Oct. 29, 2018 (DE) ............. 10 2018 218 471.2

(51) Int. Cl.
*G01R 33/54* (2006.01)
*G01R 33/48* (2006.01)
*G01R 33/483* (2006.01)
*G01R 33/561* (2006.01)
*G01R 33/58* (2006.01)

(52) U.S. Cl.
CPC ......... *G01R 33/543* (2013.01); *G01R 33/482* (2013.01); *G01R 33/4835* (2013.01); *G01R 33/5613* (2013.01); *G01R 33/58* (2013.01)

(58) Field of Classification Search
USPC ........................................................ 324/309
See application file for complete search history.

(56) References Cited

U.S. PATENT DOCUMENTS

| 5,814,990 A | * | 9/1998 | Wielopolski | G01R 33/565 324/307 |
| 2015/0035531 A1 | * | 2/2015 | Stemmer | G01R 35/005 324/309 |
| 2018/0164395 A1 | | 6/2018 | Setsompop et al. | |

OTHER PUBLICATIONS

Bilglc, Berkin et al. "Wave-CAIPI for Highly Accelerated 3D Imaging" Magnetic Resonance in Medicine, vol. 73, No. 6, pp. 2152-2162, 2015 // DOI: 10.1002/mrm.25347.
(Continued)

*Primary Examiner* — Rodney E Fuller
(74) *Attorney, Agent, or Firm* — Schiff Hardin LLP (57) ABSTRACT

Method for MR imaging of an acquisition region during a patient examination. In order to determine a point spread function, in a prior measurement for each of additional gradient output directions, the method includes choosing, in the acquisition region, a slice lying outside of an isocenter of the MR device, which slice extends in a plane perpendicular to the additional gradient output direction under consideration; following a respective slice-selective excitation of the selected slice, acquiring first calibration data using the additional gradient pulse of the additional gradient output direction under consideration, and acquiring second calibration data omitting the additional gradient pulse in each case along a k-space line, wherein a same timing sequence of additional gradient pulse and readout time window is used as in the MR sequence; and calculating, from the first and second calibration data, the point spread function for the additional gradient output direction under consideration.

9 Claims, 6 Drawing Sheets

(56) References Cited

OTHER PUBLICATIONS

Cauley, Stephen F. et al. "Autocalibrated Wave-CAIPI Reconstruction; Joint Optimization of k-Space Trajectory and Parallel Imaging Reconstruction" Magnetic Resonance in Medicine, vol. 78, No. 3, pp. 1093-1099, 2016 // DOI: 10.1002/mrm.26499.
Skope "Dynamic Field Camera—The oscilloscope for MRI" http://www.skope.swiss/dynamic-field-camera/, Jul. 9, 2018.
Breuer, Felix A. et al. "Controlled Aliasing in Volumetric Parallel Imaging (2D CAIPIRINHA)", in: Magentic Resonance in Medicine, vol. 55, pp. 549-556, DOI 10.1002/mrm.20787; 2006.
Schwarz, Jolanda Melissa et al. "GRAPPA Reconstructed Wave-CAIPI MPRAGE at 7 Tesla" Proc. Intl. Soc. Mag. Reson. Med., Abstract #5174, Apr. 2017.
Breuer, Felix A. et al. "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.

* cited by examiner

MAGNETIC RESONANCE IMAGING USING ADDITIONAL GRADIENT PULSES

BACKGROUND

The disclosure relates to a method for magnetic resonance imaging, in particular for simultaneous magnetic resonance imaging from multiple slices or for 3D imaging using undersampling along one or more phase encoding directions, of an acquisition region during an examination of a patient by means of a magnetic resonance device, wherein a magnetic resonance sequence is used which applies an additional gradient pulse of a predefined gradient shape along at least one additional gradient output direction perpendicular to a readout direction during a readout time window of the magnetic resonance sequence referred to a k-space line during Cartesian sampling, wherein a point spread function describing the actual sampling trajectory distorted by the additional gradient pulse is used in order to determine a magnetic resonance dataset from magnetic resonance signals acquired by means of the magnetic resonance sequence for the purpose of taking into account the additional gradient pulse. In addition, the disclosure relates to a magnetic resonance device, a computer program and an electronically readable data medium.

Magnetic resonance imaging has meanwhile become established as a medical imaging modality. Numerous other imaging techniques are at the same time concerned with achieving a reduction in the overall measurement time during the examination of a patient. An important starting point in this endeavor is parallel imaging. This entails in particular employing multiple receive coils in the magnetic resonance device, one proposal in connection with parallel imaging in particular having been to acquire multiple slices of an acquisition region simultaneously, which means their acquisition in a collective partial readout process following collective excitation. The corresponding imaging technique has become known in this regard as the SMS (Simultaneous Multi-Slice) imaging technique. A significant reduction in the total acquisition time is possible by this means. It is however necessary in SMS imaging to derive magnetic resonance data for the individual slices from the acquired magnetic resonance signals. During this process there exists the problem known as aliasing, and different methods have also already been proposed to deal with this phenomenon. In 2D sequences, undersampling-like artifacts are produced due to the simultaneous excitation and readout of multiple slices. The cited approaches and problems exist both in 2D and in 3D variants. In 3D variants, two phase encoding directions are used in a volume to be imaged in this case, an analogous case resulting due to undersampling in the phase encoding directions.

One well-known approach has become recognized under the name "Controlled Aliasing In Parallel Imaging Results IN Higher Acceleration" (CAIPIRINHA, frequently also called CAIPI for short), cf. in this regard for example the articles by F. Breuer et al., "Controlled aliasing in parallel imaging results in higher acceleration (CAIPIRINHA) for multi-slice imaging", Magn. Reson. Med. 53 (2005), pages 684 to 691, for the 2D application and, likewise by F. Breuer et al., "Controlled aliasing in volumetric parallel imaging (2D CAIPIRINHA)", Magn. Reson. Med. 55 (2006), pages 549-556, for the 3D application. Substantially, what happens in the 2D case is that the phase of simultaneously excited slices is modulated. This triggers shifts between the slices in the phase encoding direction between slices in which aliasing occurs, such that in this way the variation in the coil sensitivity profiles across the slices is increased and the slice dealiasing thereby improved. SMS imaging or 3D imaging with CAIPIRINHA can be employed with a large number of sequence types, such as turbo spin echo (TSE) sequences, steady-state free precession (SSFP) sequences, diffusion-weighted sequences, echoplanar imaging (EPI), and the like.

In this regard various modifications of the CAIPIRINHA method have become known in the prior art which, during a readout time window of the magnetic resonance sequence used, in addition to the gradient pulse in the readout direction, simultaneously output additional gradient pulses in additional gradient output directions perpendicular to the readout direction (i.e., in practice, the slice selection direction and the phase encoding direction) in order to achieve shifts between the simultaneously excited slices to be read out, or the volume in § D techniques, by modification of the k-space phase and encoding strategy. A particularly advantageous exemplary approach of said type has become known under the name Wave-CAIPI, in which additional sinusoidal gradient pulses are applied both along the phase encoding direction and along the slice selection direction or the other phase encoding directions, i.e. in both functional directions lying perpendicular to the readout direction, a phase shift by $\pi/2$ being inserted between the two waveforms. The result is a highly efficient k-space sampling scheme which distributes the aliasing effects uniformly in all spatial directions. Wave-CAIPI is described for example in the article by Berkin Bilgic et al., "Wave-CAIPI for Highly Accelerated 3D Imaging" Magn. Reson. Med. 73 (2015), pages 2152 to 2162.

When additional gradient pulses of said type are applied during the readout time window, the result is a modification of the k-space trajectory (gradient trajectory) specified as Cartesian sampling of a k-space line. As can be inferred for example from the cited paper by Bilgic et al., the effect of such additional gradient pulses can be understood such that each k-space line to be read out in the image described by the magnetization m(x, y, z) is convolved with a point spread function (PSF) that is dependent on the spatial position (y, z) in order to obtain the actually acquired additional gradient pulse image, in the case of sinusoidal gradient pulses for example wave[x, y, z], in formulae in Wave-CAIPI:

$$\text{wave}[x,y,z] = F_x^{-1} \text{Psf}[k,y,z] (F_x m[x,y,z]) \quad (1),$$

where $F_x$ describes the DFT operator of the readout direction (x-axis in this case) and the point spread function Psf[k,y,z] can be written as $$\text{Psf}[k,y,z] = e^{-i2\pi(P_y[k]y + P_z[k]z)} \quad (2),$$

that is, may also be understood as a product of partial point spread functions assigned to the additional gradient output directions y, z.

A problematic aspect with contemporary magnetic resonance devices, however, is that system inaccuracies, in particular in respect of the gradients, are present which can result in deviations between the nominal, i.e. desired, k-space trajectory and the actual k-space trajectory. When additional gradient pulses are used, in particular the Wave-CAIPI technique, high-quality image reconstruction is therefore only possible when a precise knowledge of the actual k-space trajectory that is described by the associated point spread function is present.

In order to obtain the k-space trajectory modified by the additional gradient pulses starting from the k-space trajectory originally specified as a Cartesian k-space line or, as the case may be, the point spread function, the article by Bilgic et al. itself proposes performing three successive measurements of the complete three-dimensional k-space without undersampling, the additional gradient pulse, in that case the Wave-CAIPI gradient pulse, being used along the phase encoding direction in the first measurement, the additional gradient pulse being used along the partition direction in the second measurement, and no additional gradient pulse being used in the third measurement. The point spread function can be calculated along the phase encoding direction (for example y) and along the slice selection direction (z) from the calibration data determined in each case. However, the measurement proposed there takes an extremely long time, in the region of 20 minutes for example. However, since the trajectory characterization finally should be performed prior to each examination of a patient in order to obtain magnetic resonance image datasets of a maximally high quality, the approach is therefore not applicable in practice because it would result in a massive extension of the overall examination time.

In an article by Stephen F. Cauley et al., "Autocalibrated Wave-CAIPI Reconstruction; Joint Optimization of k-Space Trajectory and Parallel Imaging Reconstruction", Magn. Reson. Med. 78 (2017), pages 1093 to 1099, it is proposed that a data-driven autocalibration of the point spread function be performed purely on the basis of the undersampled Wave-CAIPI k-space without collecting additional measurement data. However, the problem that exists in this regard is that a lengthy compute-intensive nonlinear optimization is necessary in order to determine the point spread function. A nonlinear optimization of said type sometimes requires several minutes on known computing devices in order to obtain clinically relevant protocols. This is disadvantageous since a time loss can follow again as a result. Furthermore, computational errors may also occur in a nonlinear optimization.

Finally, it has been proposed in an article by Jolanda Melissa Schwarz et al., "GRAPPA Reconstructed Wave-CAIPI MPRAGE at 7 Tesla", ISMRM 2017, Abstract 5174, to make use of a field camera for validation or direct measurement of the point spread function. However, the availability of a field camera represents a significant cost factor in the clinical environment which stands in the way of a widespread application. Furthermore, a new measurement would be necessary if changes are made to many acquisition parameters, in particular positioning and resolution.

SUMMARY

The object underlying the disclosure is therefore to disclose a possibility that is improved by comparison therewith, in particular one that can be performed rapidly and requires no further measurement equipment for determining a pulse spread function in the case of CAIPI methods using additional gradient pulses, in particular Wave-CAIPI.

This object is achieved by means of a method, a magnetic resonance device, a computer program and an electronically readable data medium according to the independent claims. Advantageous developments will become evident from the dependent claims.

In a method of the type cited in the introduction, it is proposed according to the disclosure that, in order to determine the point spread function, in a prior measurement for each of the additional gradient output directions:
a slice lying outside of the isocenter of the magnetic resonance device is chosen in the acquisition region, which slice extends in a plane perpendicular to the additional gradient output direction currently under consideration;

following a respective slice-selective excitation of the selected slice, first calibration data is acquired using the additional gradient pulse of the additional gradient output direction currently under consideration, and second calibration data is acquired omitting the additional gradient pulse in each case along a k-space line, the same timing sequence of additional gradient pulse and readout time window being used as in the magnetic resonance sequence; and the point spread function for the additional gradient output direction currently under consideration is calculated from the first and second calibration data.

The disclosure relates in this regard in particular to methods for simultaneous magnetic resonance imaging from multiple slices or for 3D imaging using undersampling along one or more phase encoding directions.

It should already be noted at this point that the reference to the Cartesian sampling along a k-space line relates to the basic structure of the readout module, which lasts for the readout time window, without the at least one additional gradient pulse, i.e. is defined in particular by the actual readout gradient pulse in the readout direction. Of course, the actual trajectory in the k-space is changed by the at least one additional gradient pulse away from the k-space line, as has also been explained in detail in the introduction. Nevertheless, the sampling in the k-space continues to be described for reasons of convenience on the basis of the k-space lines which would result without additional gradient pulses since the point spread functions in fact also relate to the back-transformation to precisely said k-space lines. Accordingly, the point spread function is determined in the calibration measurement, as is provided according to the disclosure, also referred to precisely said k-space line, for which the second calibration data is acquired as an unchanged trajectory. Accordingly, the present disclosure also implicitly presupposes that the acquisition is one that is specified/arranged as a Cartesian acquisition.

It is therefore proposed according to the disclosure that henceforward only a single k-space line of a single slice will be sampled for each additional gradient output direction, since these may be considered separately, in order to determine the point spread function, since it has been recognized that owing to the existing relationships said calibration data is sufficient to determine the actual k-space trajectory, and consequently the point spread function, with a high degree of precision. However, a sampling of only a single k-space line can be performed significantly faster, in particular even with repeated measurement, in just a few seconds, it furthermore being possible to perform the calculation of the point spread function from the first and second calibration data for each additional gradient output direction in an uncomplicated and rapid manner. This means, however, that the trajectory characterization can finally be performed "in vivo" prior to each examination, so that only an insignificant lengthening of the overall examination time occurs. Furthermore, no lengthy compute-intensive nonlinear optimization is necessary in order to determine the point spread function, so that savings in terms of time and computing power can be made in this case also. Compared to the use of a field camera, no dedicated additional hardware is required for the proposed approach; on the other hand, as will shortly be explained in more detail, the point spread function can simply be recalculated from the same calibration data even in the event of a change in positioning and resolution.

Since the point spread function is contrast-independent, it is particularly preferred to use a "FLASH"-like excitation and readout technique, in particular therefore a FLASH imaging technique, for the acquisition of the calibration data, which leads to time savings in particular in the case of multiple readout of the k-space lines. FLASH, in this context, stands for "Fast Angle Low Shot", that is, small excitation angles, minimum TE/TR and the use of crusher gradients after the readout operation. This results in a further fundamental difference compared to the approach according to the article by Bilgic et al., because there the same magnetic resonance sequence is used for the calibration as well as for the acquisition.

In practice, the partial point spread functions for the individual additional gradient output directions can be calculated in the following steps:

calculation of a local point spread function for a position value describing the position of the slice along the additional gradient output direction currently under consideration, in particular comprising a division of the first calibration data by the second calibration data (in the hybrid space $(k_x, y_0)$); and extrapolation of the point spread function to all position values along the additional gradient output direction currently under consideration in the acquisition region using an extrapolation relationship.

However, the extrapolation relationship mentioned is known or can be derived from the prior art, reference being made purely by way of example to the article by Berkin Bilgic et al. cited in the introduction, according to which the formula (2) describes precisely that relationship, for the point spread functions can be separated without problems according to the additional gradient output directions, in that case y and z, such that the following applies for example to the y additional gradient output direction:

$$Psf(k_x, y) = e^{iP_y(k_x)y} \quad (3)$$

Since, at a point $y_0$, the thus defined partial point spread function for the additional gradient output direction currently under consideration is known, the formula (3) can be resolved according to $P_y(k_x)$ and determine the latter, such that by using the thus determined $P_y(k_x)$ it is possible to expand the partial point spread function Psf $(k_x, y)$ to the entire acquisition region, which is to say the entire field of view (FOV).

It should generally be noted that in this case the selected slice should of course include a part of the object that is to be imaged in order to obtain meaningful calibration data. What is to be understood by the isocenter within the scope of the present disclosure is that point defined by the embodiment of the gradient coils of the gradient coil array of the magnetic resonance device at which the gradient fields have the value zero, i.e. the basic magnetic field (B0 field) is not changed by the gradient fields (Bx, By, Bz). It is therefore essential also for the present disclosure to choose the slice outside of said isocenter so that the gradients at the position of the slice (in the above example $y_0$) are not 0.

The additional gradient pulse used within the scope of the method according to the disclosure serves in this case in particular for the implementation of a CAIPI method, i.e. in particular for the uniform utilization of all spatial directions for the aliasing. In this case it is particularly preferred within the scope of the present disclosure to realize a Wave-CAIPI method through use of a sinusoidal gradient shape for the additional gradient pulse, since particular advantages are realized for this, in particular with regard to the uniform distribution and the type of convolution of the k-space trajectories, which leads to an excellent sampling strategy.

Gradient coil arrays of today's magnetic resonance devices typically comprise one gradient coil for each of three main directions/gradient directions, which means that each of the gradient coils is embodied for generating a gradient field having a gradient along its assigned gradient direction. The gradient directions are usually referred to in this context as the x-, y- and z-direction. For an actual examination, the correspondingly required functional directions (readout direction, phase encoding direction and/or slice selection direction) are beneficially assigned to the gradient directions, in particular in accordance with the desired magnetic resonance dataset in each case. For an examination of a patient, it can be provided for example that the x-direction is chosen as the readout direction, the y-direction as the phase encoding direction, and the z-direction as the slice selection direction. In this case it is common practice, for example in the Wave-CAIPI method, to use both available additional gradient output directions, i.e. both the phase encoding direction and the slice selection direction.

A corresponding assignment of functional directions to gradient directions is also provided within the scope of the calibration measurements, notwithstanding the fact that a different assignment is chosen depending on the additional gradient output direction currently under consideration. In other words, a suitable assignment of functional directions of the calibration sequence used for the acquisition of the calibration data takes place for each of the at least one additional gradient readout directions defined as one of the gradient directions for which a gradient coil of the gradient coil array of the magnetic resonance device is present. In practice, the additional gradient output direction currently under consideration is chosen in this case as the slice selection direction, and the readout direction and the phase encoding direction are chosen as gradient directions perpendicular thereto, the readout direction being chosen in particular in the case of two additional gradient output directions as perpendicular to both additional gradient output directions, i.e. as in the case of the magnetic resonance sequence used for the actual acquisition of the magnetic resonance dataset.

The present disclosure can be applied to any sequence type of magnetic resonance sequences, for example all 3D sequences (e.g. GRE sequences, TurboFLASH (TFL), SPACE (3D-TSE), TSE sequences, EPI sequences, and others. The only prerequisite is that on the one hand a Cartesian sampling of the k-space is specified, and on the other hand the calibration sequence is synchronized with the magnetic resonance sequence, in concrete terms the timing sequence of readout time window (analog-to-digital converter (ADC) active) and additional gradient pulses is exactly the same as that of the magnetic resonance sequence. No time offset must therefore occur in the calibration sequence compared with the magnetic resonance sequence.

In an advantageous development of the present disclosure it can be provided that the k-space line that is to be read out from the selected slice is chosen as a k-space line intersecting the k-space center (of the selected slice). From this, there results the advantage that the maximum possible signal-to-noise ratio is present along said center line in the k-space. If the slice is situated in the z-x plane, the k-space line at $k_z=0$ is therefore chosen.

It is particularly preferred within the scope of the present disclosure if the acquisition of the first and the second calibration data is repeated several times for statistical combination purposes, in particular averaging. Averaging is to be understood in this context broadly as a statistical derivation of a calibration data item that is to be used. For example, a weighted averaging and/or an outlier detection can take place. In this way, measured calibration data of multiple repetitions can be averaged in order to obtain the first and second calibration data that are finally to be used. Since the readout of a single k-space line is possible extremely quickly, this advantageously does not result in a significant lengthening of the measurement time of said calibration measurement. Furthermore, an improvement in the signal-to-noise ratio, and consequently in the accuracy of the point spread function, is achieved as a result of the averaging over multiple individual measurement operations.

In a development of the disclosure it can furthermore be provided that a slice spaced at the furthest possible distance from the isocenter and containing a part of the object is selected in the acquisition region. In this way, the greatest possible gradient amplitudes are achieved within the selected slice, which in turn likewise contributes to a high-quality measurement of the point spread function. It should be mentioned at this point that the slice thickness also represents an optimizable parameter. A higher slice thickness improves the signal-to-noise ratio but reduces the precision of the extrapolation, since a discrete position of the slice is expected, but not a continuum.

It is furthermore advantageous if a recalculation of the point spread function is performed without reacquisition of calibration data in the event of a change in the resolution outside of the readout direction for the examination that is to be carried out and/or in the event of a change in the position of the acquisition region. Owing to the hereinabove already described extrapolation to the entire acquisition region, the approach according to the disclosure requires no repeat measurement when acquisition parameters relating to the positioning and/or the resolution outside of the readout direction are changed, since in this case the point spread function can simply be recalculated. There is no need to repeat calibration measurements.

In addition to the method, the present disclosure also relates to a magnetic resonance device, comprising a control device embodied to perform the inventive method. All statements made in relation to the inventive method may be applied analogously to the inventive magnetic resonance device. In this case the control device may include in particular at least one processor and/or a storage means. Functional units of such a control device may comprise a selection unit for slice selection and a calculation unit for calculating the point spread function in addition to the sequence unit which is already provided anyway and which controls the acquisition operation on the basis of the magnetic resonance sequence and the calibration sequence.

An inventive computer program can for example be loaded directly into a memory of a control device of a magnetic resonance device and has program means for performing the steps of an inventive method when the computer program is executed in the control device of the magnetic resonance device. The computer program may be stored on an inventive electronically readable data medium, which therefore comprises electronically readable control information stored thereon, which control information comprises at least one inventive computer program and is embodied in such a way that it performs an inventive method when the data medium is used in a control device of a magnetic resonance device.

BRIEF DESCRIPTION OF THE FIGURES

Further advantages and details of the present disclosure will become apparent from the exemplary embodiments described below, as well as with reference to the drawings, in which.

DETAILED DESCRIPTION

An exemplary embodiment of the present disclosure for an examination of a patient by means of a magnetic resonance device is presented in the following, which magnetic resonance device comprises, as is generally known, a gradient coil array having three gradient coils, each of which is assigned to one of the three gradient directions: the x-direction, the y-direction and the z-direction. SMS imaging using Wave-CAIPI is to be employed to accelerate the process during the acquisition of the magnetic resonance dataset in an acquisition region of the patient, which region contains for example the head of the patient as examination object; the sequence type of the magnetic resonance sequence used for this is not significant in this case. Alternatively to SMS imaging, a 3D imaging technique using undersampling along both phase encoding directions may also be employed. In the present example, the readout direction for the acquisition of the magnetic resonance signals to be evaluated for producing the magnetic resonance dataset by means of the magnetic resonance sequence is to be the x-direction, which means that additional sine-shaped gradient pulses (Wave-CAIPI pulses) which are offset relative to one another by $\pi/2$ are output along the y-direction and the z-direction (phase encoding direction and slice selection direction). As is generally known, in order to derive the magnetic resonance dataset correctly from the magnetic resonance data, a point spread function is used to take into account the effects of the additional gradient pulses, i.e. for the back-calculation onto the actually specified k-space lines in the Cartesian sampling scheme, the determination of which point spread function being the central concern of the method described hereinbelow.

The examination is prepared in a step S1, which means that the following are known upon completion of step S1: the readout direction (the x-direction in this case) when using the magnetic resonance sequence, the additional gradient output directions (the y-direction and z-direction in this case) and the timing sequence in the readout module of the magnetic resonance sequence, in particular therefore the location of the readout time window and the precise timing sequence of the additional gradient pulses related thereto.

In a step S2, a calibration process for determining the point spread function then begins, which process is performed twice in the present example, once for each additional gradient output direction. To that end, an additional gradient output direction is selected in the first instance, initially the y-direction in the exemplary embodiment explained in more detail here, in order, in a step S2, to choose a slice extending perpendicularly to said additional gradient output direction currently under consideration and to select an assignment of gradient directions to functional directions of a calibration sequence. This is explained in more detail on the basis of the illustration shown in FIG. 2. There, the acquisition region 1 is indicated schematically, as also is the coordinate system 2 of the gradient directions x, y and z. As can be seen, the additional gradient output direction 3 currently under consideration corresponds to the y-direction. Accordingly, the y-direction is chosen as the slice selection direction (SL) in the present instance. As in the case of the magnetic resonance sequence, the readout direction (RO) is chosen as the x-direction, the phase encoding direction (PE) consequently being chosen as the z-direction.

Figure 2:
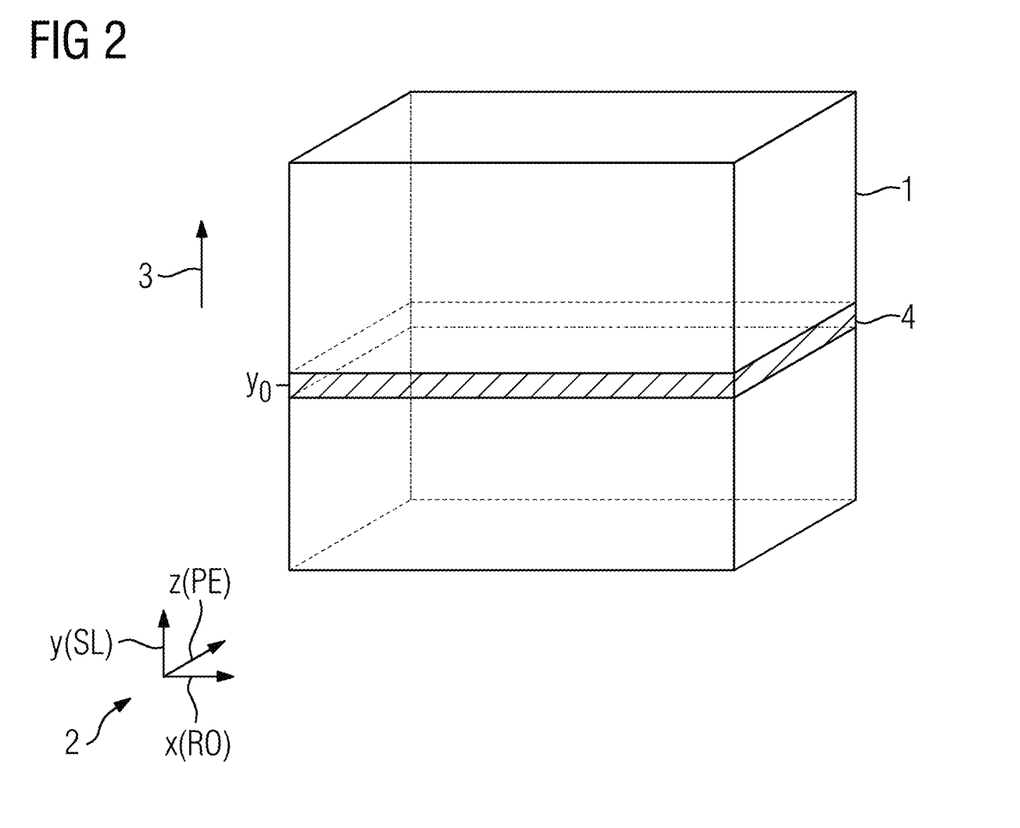
FIG. 2 shows an assignment of functional directions to gradient directions for a first additional gradient output direction.

A slice 4 is now selected which is located at a position $y_0$, which is situated at a distance from the isocenter of the magnetic resonance device, in particular at a maximum at such a distance that there is nonetheless still a sufficient amount of the object to be examined, for example the head, included in the slice 4.

Figure 3:
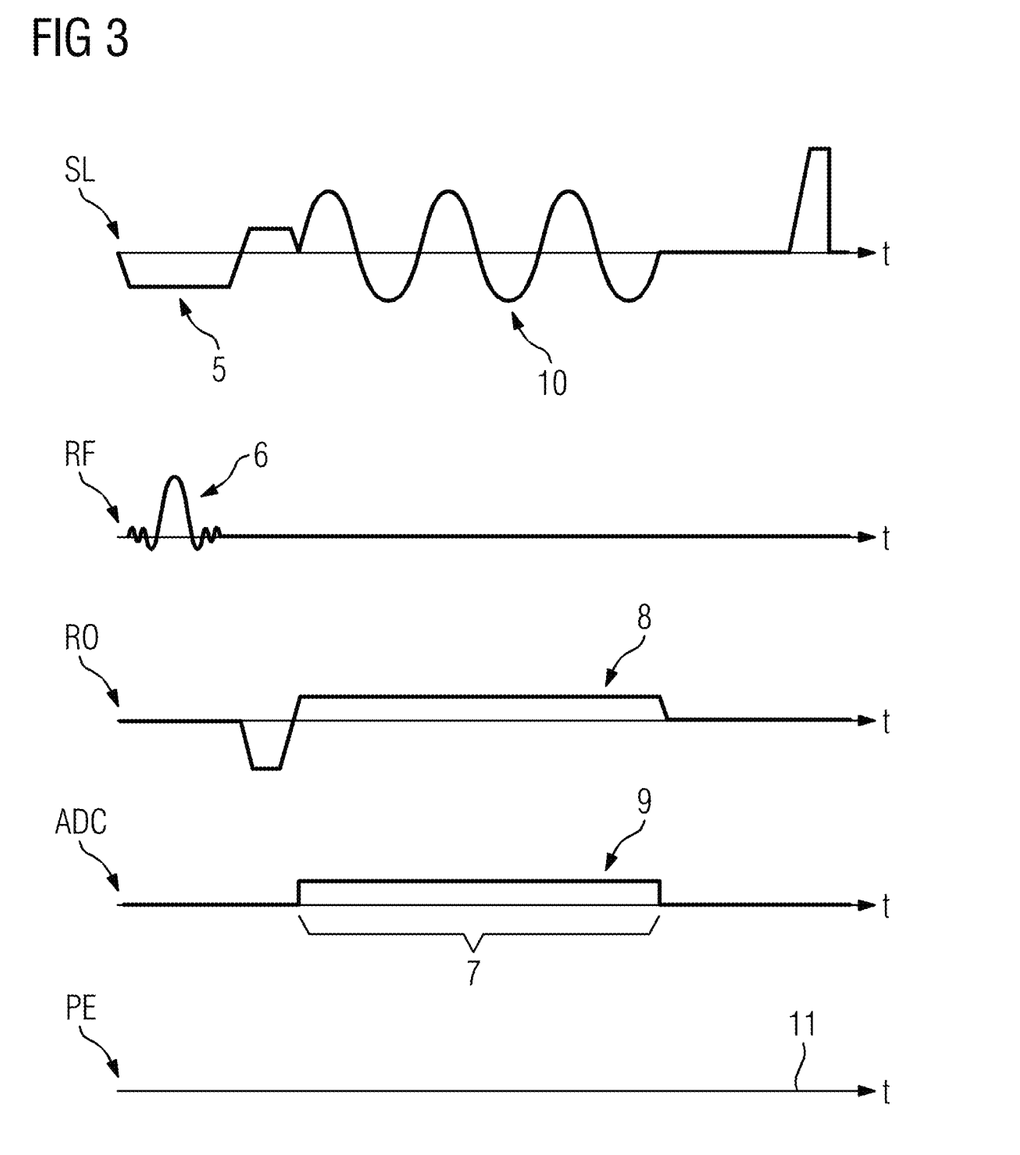
FIG. 3 shows a sequence diagram for the acquisition of first calibration data.

In the further course of step S2, first calibration data is then acquired initially by means of the sequence diagram shown in FIG. 3. As can be seen, a slice-selective, cf. slice selection gradient pulse 5, excitation, cf. excitation pulse 6, of the slice 4 is accordingly performed initially. The first calibration data is then acquired in a readout time window 7, cf. readout gradient pulse 8 and ADC opening 9, corresponding in its length to the readout time window of the magnetic resonance sequence that is to be used later. In exactly the same timing sequence as in the case of the magnetic resonance sequence, the additional sinusoidal gradient pulse 10 is output along the slice selection direction, though in the present case only in said direction since no additional gradient pulses are provided for the phase encoding direction, cf. bottom graph 11, which corresponds to the other additional gradient output direction.

Figure 4:
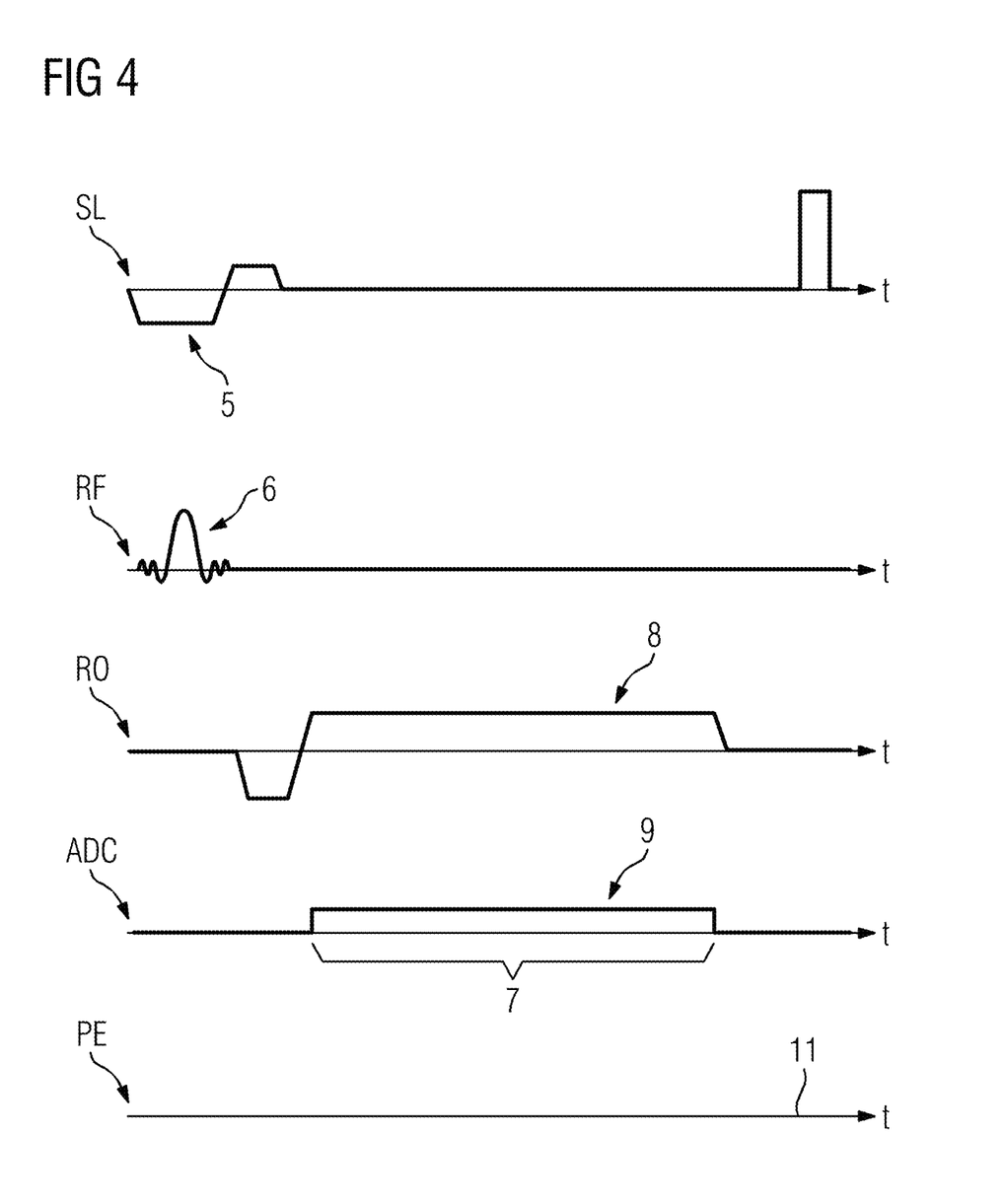
FIG. 4 shows a sequence diagram for the acquisition of second calibration data.

In a further substep of step S2, second calibration data is then acquired in accordance with the sequence diagram of FIG. 4, in which the only difference from the sequence diagram in FIG. 3 is the absence of the additional gradient pulse 10.

In the present example, only a single k-space line (of course convolved by the additional gradient pulse 10 in the case of the first calibration data) is acquired here by means of the calibration sequences of FIG. 3 and FIG. 4, which k-space line is specified as extending through the k-space center of the slice 4 ($k_z$=0), since that is where the maximum signal-to-noise ratio is present. However, this one k-space line is sampled repeatedly in order to obtain the first and second calibration data for the additional gradient output direction 3 currently under consideration by means of statistical averaging.

In a step S3, the first and second calibration data are then used in order to determine the point spread function for the additional gradient output direction 3 (y-direction) currently under consideration. In the course thereof, the point spread function for the position $y_0$ is determined in the first instance by comparison of the first and the second calibration data, in particular comprising a division. From this, the point spread function can then be extrapolated to arbitrary values of y by using the relationship (3), where initially (3) is resolved according to $P_y(k_x)$, and $y_0$ and also the point spread function known there are used. With the thus determined $P_y(k_x)$, the general point spread function for different values of y can then be obtained, if required, by inserting the required values of y in (3).

Figure 1:
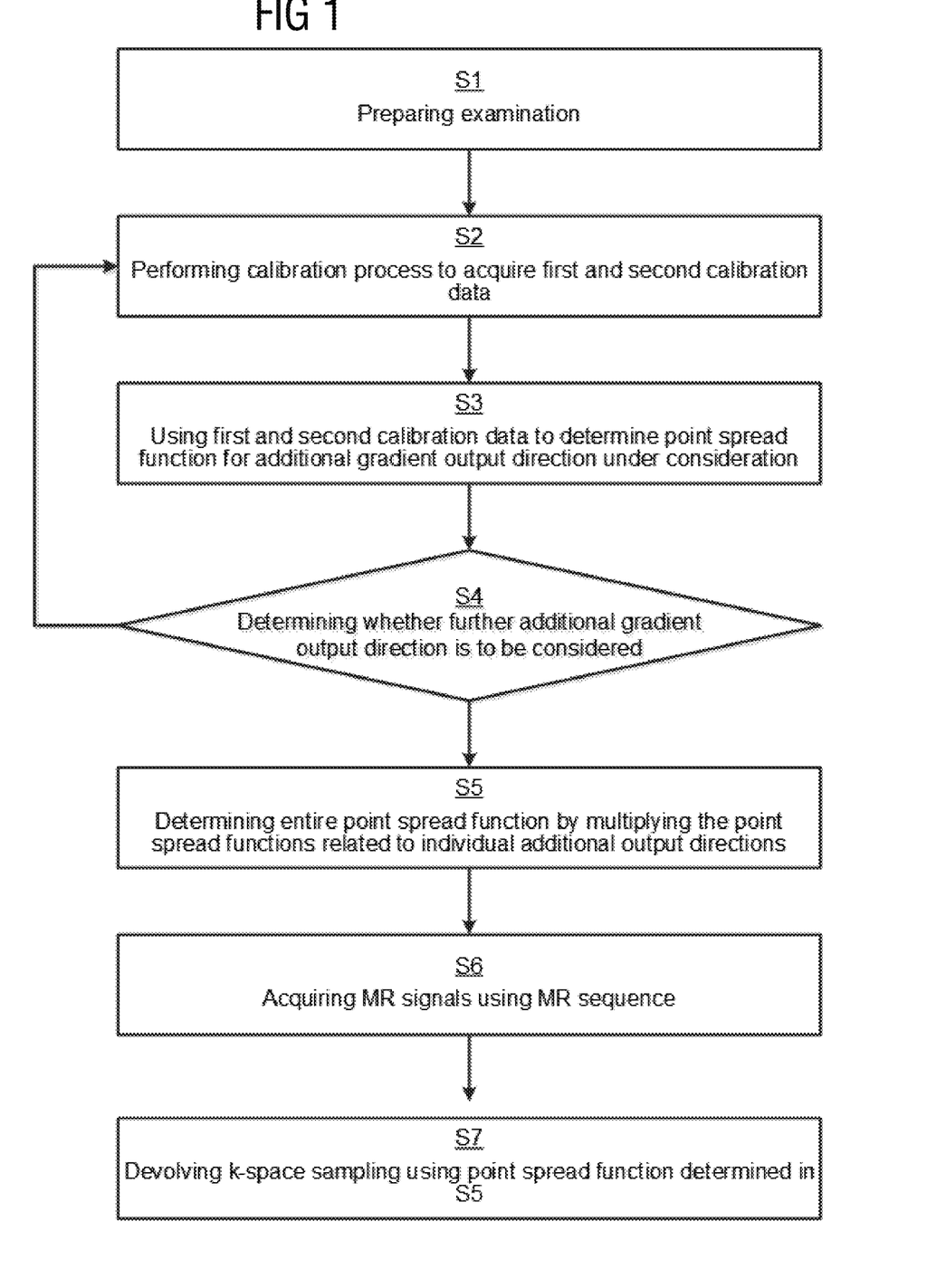
FIG. 1 shows a flowchart of an exemplary embodiment of the method according to the disclosure.
Figure 5:
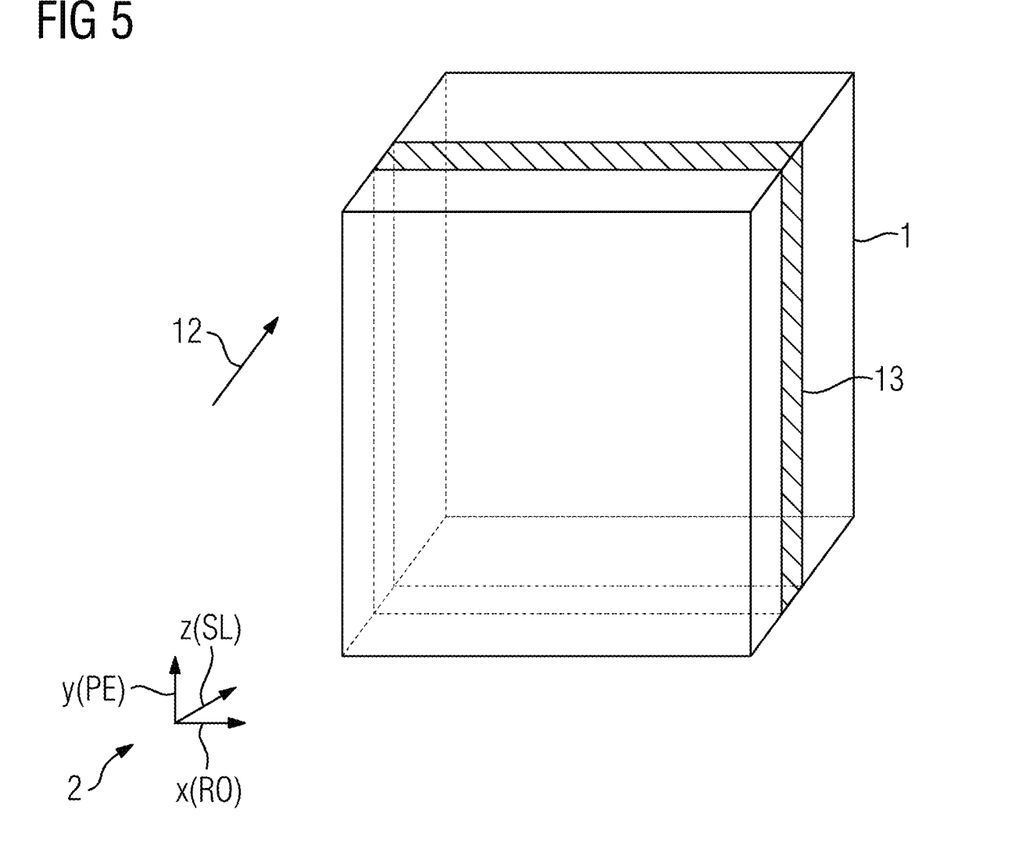
FIG. 5 shows an assignment of functional directions to gradient directions for a second additional gradient output direction.

In a step S4, cf. FIG. 1 once again, a check is then carried out to determine whether a further additional gradient output direction is to be considered, which applies in the present case, namely the z-direction. Accordingly, a branch back to step S2 is made with a new additional gradient output direction 12 currently under consideration, cf. FIG. 5. According to the new additional gradient output direction 12 currently under consideration, the functional directions of the calibration sequence are now reassigned to the gradient directions, cf. coordinate system 2, where in the present example the x-direction again forms the readout direction, the z-direction the slice selection direction, and the y-direction the phase encoding direction. A corresponding new slice 13, which now extends in the x-y plane, is selected in accordance with the criteria discussed in relation to FIG. 2. There then follows, once again using the calibration sequences analogously to FIG. 3 and FIG. 4, the measurement of first and second calibration data for the additional gradient output direction 12 currently under consideration, the additional gradient pulse 10 assigned to the z-direction being output this time, though no longer the additional gradient pulse 10 assigned to the y-direction.

In a repeat pass through step S3, the point spread function is accordingly determined for the z-direction as additional gradient output direction 12.

In a then following step S5, however, after all additional gradient output directions 3, 12 have been processed, this also allows the entire point spread function, cf. formula (2), to be easily determined by multiplication of the point spread functions related to the individual additional gradient output directions 3, 12.

In a step S6, the magnetic resonance signals are then acquired by means of the magnetic resonance sequence, after which, in a step S7, the point spread function determined in step S5 is used in order to deconvolve the k-space sampling correctly and enable a high-quality magnetic resonance dataset to be determined.

Figure 6:
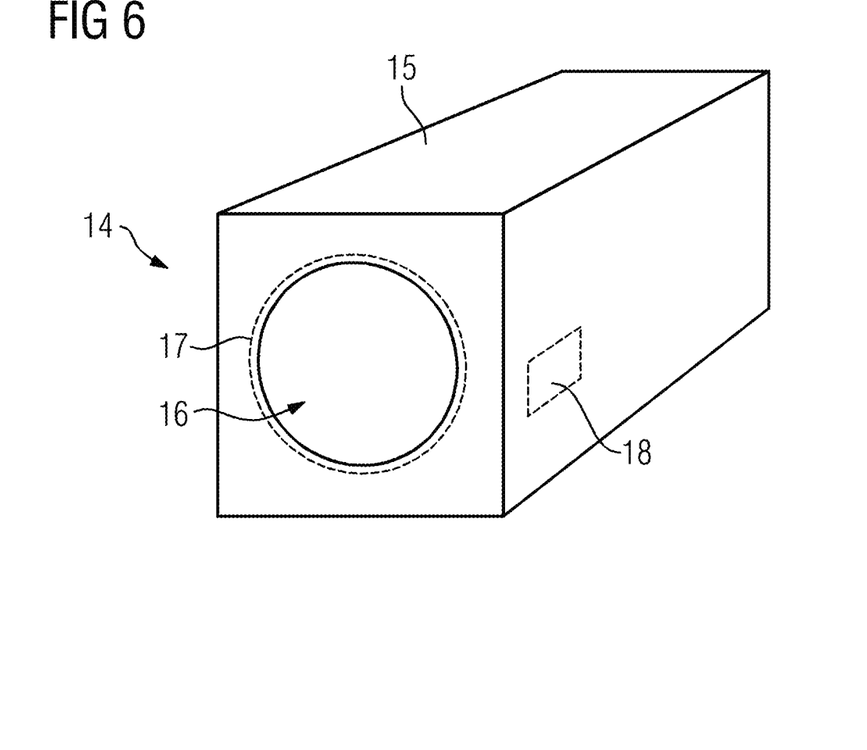
FIG. 6 shows a schematic diagram of a magnetic resonance device according to the disclosure.

FIG. 6 shows a schematic diagram of a magnetic resonance device 14 according to the disclosure, which, as is generally known, comprises a main magnet unit 15 that defines a patient receiving zone 16 around which the gradient coil array 17 (merely indicated here) comprising the three gradient coils extends. The operation of the magnetic resonance device 14 is controlled by means of a control device 18, which is also embodied to perform the method according to the disclosure.

Figure 7:
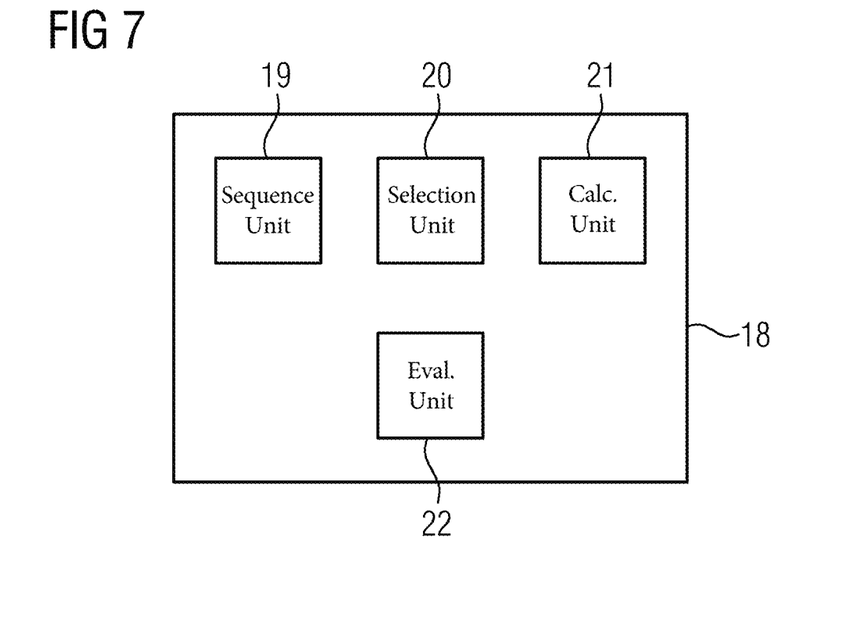
FIG. 7 shows the functional layout of a control device.

For this purpose, the control device 18, cf. FIG. 7, comprises, in addition to a generally known sequence unit 19, which is used for actuating the different components of the magnetic resonance device 14 in order to implement the calibration sequence and the magnetic resonance sequence, firstly a selection unit 20 for performing the assignment and slice selection measures of step S2. The control device 19 further comprises a calculation unit 21 for determining the point spread function from the first and second calibration data according to steps S3 and S5. The correspondingly determined point spread function is used in an evaluation unit 22 in order to enable a correct reconstruction of the magnetic resonance dataset.

Although the disclosure has been illustrated and described in greater detail on the basis of the preferred exemplary embodiment, the disclosure is not limited by the disclosed examples and other variations may be derived herefrom by the person skilled in the art without leaving the scope of protection of the disclosure.

The invention claimed is:

1. A method for magnetic resonance imaging of an acquisition region during an examination of a patient by means of a magnetic resonance device, using a magnetic resonance sequence which applies an additional gradient pulse of a predefined gradient shape along at least one additional gradient output direction perpendicular to a readout direction during a readout time window of the magnetic resonance sequence referred to a k-space line during Cartesian sampling, using a point spread function describing an actual sampling trajectory distorted by the additional gradient pulse in order to determine a magnetic resonance dataset from magnetic resonance signals acquired by means of the magnetic resonance sequence to take into account the additional gradient pulse, wherein in order to determine the point spread function, in a prior measurement for each of the additional gradient output directions, the method comprising:

choosing, in the acquisition region, a slice lying outside of the isocenter of the magnetic resonance device, which slice extends in a plane perpendicular to the additional gradient output direction under consideration;

following a respective slice-selective excitation of the selected slice, acquiring first calibration data using the additional gradient pulse of the additional gradient output direction under consideration, and acquiring second calibration data omitting the additional gradient pulse in each case along a k-space line, wherein a same timing sequence of additional gradient pulse and readout time window is used as in the magnetic resonance sequence; and     calculating, from the first and second calibration data, the point spread function for the additional gradient output direction under consideration.

2. The method as claimed in claim 1, further comprising:
    realizing a Wave-CAIPI method by using a sinusoidal gradient shape for the additional gradient pulse.

3. The method as claimed in claim 1, further comprising:
    choosing the k-space line that is to be read out from the selected slice as a k-space line intersecting the k-space center.

4. The method as claimed in claim 1, further comprising:
    repeating the acquisition of the first and second calibration data multiple times for statistical combining.

5. The method as claimed in claim 1, further comprising:
    selecting, in the acquisition region, a slice spaced at a furthest possible distance from the isocenter and containing a part of the object.

6. The method as claimed in claim 1, further comprising recalculating the point spread function without reacquisition of calibration data if there is a change in a resolution for the examination that is to be carried out or a change in a position of the acquisition region.

7. The method as claimed in claim 1, wherein the acquisition of the first and second calibration data comprises a FLASH imaging technique.

8. A magnetic resonance device, comprising:
    a controller configured to perform the method as claimed in claim 1.

9. A non-transitory computer-readable medium comprising a computer program for performing the steps of the method of claim 1, when executed on a control device of a magnetic resonance device.

* * * * *